United States Patent
Suzuki et al.

(10) Patent No.: US 9,617,492 B2
(45) Date of Patent: Apr. 11, 2017

(54) COMPLEX POLYESTER COMPOSITION, LUBRICANT COMPOSITION, LUBRICANT, AND PRODUCTION METHOD FOR COMPLEX POLYESTER COMPOSITION

(71) Applicant: FUJIFILM Corporation, Tokyo (JP)

(72) Inventors: Hiroyuki Suzuki, Ashigarakami-gun (JP); Yuji Terada, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/010,731

(22) Filed: Jan. 29, 2016

(65) Prior Publication Data

US 2016/0145525 A1    May 26, 2016

Related U.S. Application Data

(63) Continuation of application No. PCT/JP2014/070056, filed on Jul. 30, 2014.

(30) Foreign Application Priority Data

Jul. 31, 2013  (JP) .................................. 2013-159830

(51) Int. Cl.

| | |
|---|---|
| *C10M 173/02* | (2006.01) |
| *C07C 69/34* | (2006.01) |
| *C07C 69/52* | (2006.01) |
| *C10M 129/78* | (2006.01) |
| *C08G 63/12* | (2006.01) |
| *C10M 105/46* | (2006.01) |
| *C08G 63/553* | (2006.01) |
| *C10M 107/32* | (2006.01) |
| *C07C 67/08* | (2006.01) |
| *C07C 69/602* | (2006.01) |
| *C08G 63/52* | (2006.01) |
| *C08G 63/547* | (2006.01) |
| *C08G 63/676* | (2006.01) |
| *C08G 63/78* | (2006.01) |
| *C10M 101/02* | (2006.01) |
| *C10M 125/22* | (2006.01) |

(52) U.S. Cl.
CPC ........... *C10M 129/78* (2013.01); *C07C 67/08* (2013.01); *C07C 69/602* (2013.01); *C08G 63/12* (2013.01); *C08G 63/52* (2013.01); *C08G 63/547* (2013.01); *C08G 63/553* (2013.01); *C08G 63/676* (2013.01); *C08G 63/78* (2013.01); *C10M 101/02* (2013.01); *C10M 105/46* (2013.01); *C10M 107/32* (2013.01); *C10M 125/22* (2013.01); *C10M 2203/1006* (2013.01); *C10M 2205/0285* (2013.01); *C10M 2207/0406* (2013.01); *C10M 2207/2815* (2013.01); *C10M 2207/2825* (2013.01); *C10M 2207/2835* (2013.01); *C10M 2207/2845* (2013.01); *C10M 2207/2855* (2013.01); *C10M 2207/3045* (2013.01); *C10M 2207/401* (2013.01); *C10M 2209/1023* (2013.01); *C10M 2213/0606* (2013.01); *C10M 2229/025* (2013.01); *C10N 2230/06* (2013.01); *C10N 2240/02* (2013.01); *C10N 2240/08* (2013.01); *C10N 2240/10* (2013.01); *C10N 2240/12* (2013.01); *C10N 2240/121* (2013.01); *C10N 2240/30* (2013.01); *C10N 2240/40* (2013.01); *C10N 2240/401* (2013.01); *C10N 2240/402* (2013.01); *C10N 2250/10* (2013.01); *C10N 2250/18* (2013.01)

(58) Field of Classification Search
CPC ....... C10M 2207/282; C10M 2207/304; C07C 2101/14
USPC .......................... 508/455, 492; 560/193, 199
See application file for complete search history.

(56) References Cited

U.S. PATENT DOCUMENTS

| | | | |
|---|---|---|---|
| 5,503,762 A * | 4/1996 | Bongardt ............. | C10M 105/42 508/481 |
| 5,854,185 A | 12/1998 | Roth et al. | |
| 2007/0190001 A1 | 8/2007 | Jacques et al. | |
| 2012/0184474 A1* | 7/2012 | Kawata ................... | C07C 67/08 508/497 |

FOREIGN PATENT DOCUMENTS

| | | |
|---|---|---|
| JP | 8-208814 A | 8/1996 |
| JP | 2002-97482 A | 4/2002 |
| JP | 2005-154726 A | 6/2005 |
| JP | 2005-213377 A | 8/2005 |

(Continued)

OTHER PUBLICATIONS

Extended European Search Report, dated Jun. 13, 2016, for European Application No. 14832795.0.

(Continued)

*Primary Examiner* — Vishal Vasisth
(74) *Attorney, Agent, or Firm* — Birch, Stewart, Kolasch & Birch, LLP

(57) ABSTRACT

An object of the present invention is to provide a lubricant which has excellent lubrication performance and is able to exhibit excellent lubrication performance even when under extreme pressure conditions. The present invention relates to a complex polyester composition containing polyester obtained by condensing polyhydric alcohol having at least two hydroxyl groups, a dicarboxylic acid having 44 carbon atoms, and monohydric alcohol. Further, the present invention relates to a lubricant composition containing the complex polyester composition, and a lubricant and a production method for a complex polyester composition.

22 Claims, No Drawings

(56) References Cited

FOREIGN PATENT DOCUMENTS

| JP | 2005-232434 A | 9/2005 |
| JP | 2005-232470 A | 9/2005 |
| JP | 2007-217414 A | 8/2007 |
| JP | 2011-89106 A | 5/2011 |

OTHER PUBLICATIONS

International Preliminary Report on Patentability with English translation, dated Feb. 11, 2016, issued in PCT/JP2014/070056 (Forms PCT/IB/338, PCT/IB/373, PCT/ISA/237 and PCT/IB/326).
International Search Report, issued in PCT/JP2014/070056, dated Aug. 26, 2014.
Written Opinion of the International Searching Authority, issued in PCT/JP2014/070056, dated Aug. 26, 2014.
Chinese Office Action and Search Report dated Aug. 2, 2016, for Chinese Application No. 201480039929.3.
Feng et al., "Synthesis and defoaming performance of polyester by condensation of C36 dimer fatty acid and PEG/PPG with oleic acid as end block," China Surfactant Detergent & Cosmetics, vol. 36. No. 2, Apr. 2006, pp. 76-80 with the English abstract.
English translation of the Chinese Office Action and Search Report dated Aug. 2, 2016, for Chinese Application No. 201480039929.3.

* cited by examiner

COMPLEX POLYESTER COMPOSITION, LUBRICANT COMPOSITION, LUBRICANT, AND PRODUCTION METHOD FOR COMPLEX POLYESTER COMPOSITION

CROSS-REFERENCE TO RELATED APPLICATIONS

This application is a Continuation of PCT International Application No. PCT/JP2014/070056, filed on Jul. 30, 2014, which claims priority under 35 U.S.C. Section 119(a) to Japanese Patent Application No. 2013-159830 filed on Jul. 31, 2013. Each of the above applications is hereby expressly incorporated by reference, in its entirety, into the present application.

BACKGROUND OF THE INVENTION

1. Field of the Invention

The present invention relates to a complex polyester composition and a lubricant. Specifically, the present invention relates to a complex polyester composition containing specific polyester, and a lubricant containing the complex polyester composition.

2. Description of the Related Art

In general, a lubricant contains base oil and various additives. Examples of the base oil include mineral oil obtained from crude oil, ester-based oil which is chemically synthesized, fluorine oil, polyalphaolefin-based oil, and the like. Among them, the ester-based oil is preferably used in a jet plane, automobile engine oil, grease, and the like from the viewpoints of a low fluid point, a high viscosity index, a high flash point, excellent lubrication performance, biodegradability, and the like.

Various esters such as monoester obtained from a reaction between an aliphatic monocarboxylic acid and monohydric alcohol; diester obtained from a reaction between an aliphatic dibasic acid and monohydric alcohol; ester obtained from a reaction between polyhydric alcohol and an aliphatic carboxylic acid; and complex ester obtained from a reaction between polyol, a polybasic acid, and an aliphatic monocarboxylic acid, have been disclosed as the ester-based oil (JP2002-097482A, JP2005-154726A, JP2005-232434A, JP2005-213377A, and JP2005-232470A).

In addition, in JP2007-217414A, JP1996-208814A (JP-H08-208814A), and JP2011-89106A, a polyester composition obtained from a reaction between an aliphatic dibasic acid and polyol is disclosed. In JP2007-217414A, ester obtained from a reaction between polyol and an aliphatic diacid dimer is disclosed. Here, ester to be obtained is used as a cosmetic composition.

In addition, in JP1996-208814A (JP-H08-208814A), ester obtained from a reaction between polyol, a fatty acid, and a dibasic acid is disclosed, and in JP2011-89106A, ester obtained from a reaction between polyol, a dibasic acid, and monohydric alcohol is disclosed. In this literature, ester to be obtained is able to be used as a lubricant composition and is able to exhibit excellent lubrication performance.

SUMMARY OF THE INVENTION

Recently, the lubricant has been required to have high lubrication performance according to diversification and advancement of the industrial field. For this reason, development of a polyester composition having low friction properties and excellent lubrication performance has progressed. Further, the polyester composition has been required to exhibit excellent lubrication performance even in rigorous conditions according to rigorous use conditions of the lubricant.

However, according to the studies of the present inventors, it is obvious that the lubricant containing the ester disclosed in JP2007-217414A and JP1996-208814A (JP-H08-208814A) is not able to sufficiently exhibit necessary lubrication performance under rigorous conditions. For this reason, under rigorous conditions such as a condition of being under extreme pressure, further enhancement such as exhibiting of sufficient lubrication performance has been required.

In addition, according to the studies of the present inventors, it is obvious that the lubricant containing the ester disclosed in JP2011-89106A is able to exhibit a certain level of lubrication performance, but the transparency of the lubricant decreases. In such a lubricant having low transparency, it is difficult to determine the degree to which the deterioration of the lubricant has progressed, and it may be difficult to determine that foreign substances are mixed into the lubricant.

Therefore, in order to solve such problems of the related art and to provide a lubricant which has excellent lubrication performance and is able to exhibit excellent lubrication performance even when under extreme pressure conditions, the present inventors have carried out research. Further, in order to provide a lubricant having high transparency in which it is possible to easily determine the degree to which the deterioration of the lubricant has progressed or whether or not foreign substances are mixed into the lubricant, the present inventors have carried out research.

As a result of intensive studies for attaining the objects described above, the present inventors have found that it is possible to exhibit excellent lubrication performance under extreme pressure conditions by obtaining a complex polyester composition containing specific polyester. Furthermore, the specific polyester is polyester which is obtained by condensing polyhydric alcohol having at least two hydroxyl groups, a dicarboxylic acid having 44 carbon atoms, and monohydric alcohol. Further, the present inventors have found that it is possible to obtain a lubricant having high transparency by using the complex polyester composition containing such polyester, and have completed the present invention.

Specifically, the present invention has the following configurations.

[1] A complex polyester composition containing polyester obtained by condensing polyhydric alcohol having at least two hydroxyl groups, a dicarboxylic acid having 44 carbon atoms, and monohydric alcohol.

[2] The complex polyester composition according to [1], in which the dicarboxylic acid having 44 carbon atoms is an erucic acid dimer.

[3] The complex polyester composition according to [1] or [2], in which the polyhydric alcohol has three or more hydroxyl groups.

[4] The complex polyester composition according to any one of [1] to [3], in which the polyhydric alcohol is selected from pentaerythritol, trimethylol propane, glycerin, or dipentaerythritol.

[5] The complex polyester composition according to any one of [1] to [4], in which the monohydric alcohol is denoted by General Formula (1) described below.

$$R^a\text{---}(O(CX^{a1}X^{a2})_{na1})_{na2}OH \qquad \text{General Formula (1)}$$

In General Formula (1), $R^a$ represents an alkyl group which may have a substituent group, a cycloalkyl group which may have a substituent group, an alkenyl group which may have a substituent group, an aryl group which may have a substituent group, or a heteroaryl group which may have a substituent group, and $X^{a1}$ and $X^{a2}$ each independently represent a hydrogen atom, a halogen atom, or an alkyl group. In addition, na1 represents an integer of 2 to 4, and na1 represents an integer of 1 to 12.

[6] The complex polyester composition according to any one of [1] to [5], in which the complex polyester composition contains polyester obtained by further condensing a dimer acid in addition to the polyhydric alcohol, the dicarboxylic acid having 44 carbon atoms, and the monohydric alcohol.

[7] The complex polyester composition according to any one of [1] to [6], in which the complex polyester composition contains polyester obtained by further condensing a trimer acid in addition to the polyhydric alcohol, the dicarboxylic acid having 44 carbon atoms, and the monohydric alcohol.

[8] The complex polyester composition according to [1], in which at least one type of polyester is denoted by General Formula (2) described below.

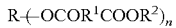  General Formula (2)

In General Formula (2), R represents a n-valent atomic group, $R^1$ represents a residue of a dicarboxylic acid having 44 carbon atoms, and $R^2$ represents an alkyl group which may have a substituent group, a cycloalkyl group which may have a substituent group, an alkenyl group which may have a substituent group, an aryl group which may have a substituent group, or a heteroaryl group which may have a substituent group. In addition, n represents an integer of 2 to 6.

[9] The complex polyester composition according to [8], in which in General Formula (2) described above, n represents an integer of 3 to 6.

[10] The complex polyester composition according to [8] or [9], in which in General Formula (2) described above, R represents an atomic group formed of saturated aliphatic hydrocarbon which may have a substituent group.

[11] The complex polyester composition according to any one of [8] to [10], in which in General Formula (2) described above, the number of carbon atoms of $R^2$ is greater than or equal to 4.

[12] The complex polyester composition according to any one of [8] to [11], in which in General Formula (2) described above, $R^2$ represents a group having an oxyalkylene structure.

[13] The complex polyester composition according to any one of [1] to [12], in which viscosity at 40° C. is 50 mPa·s to 1650 mPa·s.

[14] A lubricant composition containing the complex polyester composition according to any one of [1] to [13], and one type or two or more types of additives selected from an abrasion preventing agent, a viscosity index improver, an antioxidant, a cleaning agent, a dispersant, a fluidizing agent, a curing agent, a corrosion preventing agent, a seal compatible agent, a defoaming agent, a rust preventing agent, a friction adjuster, and a thickener.

[15] A lubricant composition containing at least the complex polyester composition according to any one of [1] to [13] or the lubricant composition according to [14], and one type or two or more types of mediums selected from mineral oil, a fatty oil compound, polyolefin oil, silicone oil, perfluoropolyether oil, diphenyl ether oil, aromatic ester oil, aliphatic monoester oil, aliphatic diester oil, and polyol ester lubricating oil.

[16] A lubricant containing the complex polyester composition according to any one of [1] to [13] or the lubricant composition according to [14] or [15].

[17] The lubricant according to [16], in which the lubricant is used as lubricating oil for grease, a releasing agent, engine oil for an internal combustion engine, oil for metal working (machining), oil for a bearing, fuel for a combustion engine, vehicle engine oil, gear oil, operating oil for an automobile, lubricating oil for a vessel and an aircraft, machine oil, turbine oil, hydraulic operating oil, compressor and vacuum pump oil, freezer oil, lubricating oil for metal working, a lubricant for magnetic recording medium, a lubricant for a micro machine, a lubricant for an artificial bone, shock absorber oil, or rolling oil.

[18] A production method for a complex polyester composition including a step of obtaining a mixture by mixing polyhydric alcohol having at least two hydroxyl groups, a dicarboxylic acid having 44 carbon atoms, and monohydric alcohol; and a step of performing dehydration condensation with respect to the mixture.

[19] The production method for a complex polyester composition according to [18], in which the step of obtaining the mixture is a step of mixing the polyhydric alcohol the dicarboxylic acid having 44 carbon atoms, and the monohydric alcohol such that an equivalence ratio of mixing the dicarboxylic acid having 44 carbon atoms with respect to the polyhydric alcohol is 1 to 3, and an equivalence ratio of mixing the monohydric alcohol with respect to the polyhydric alcohol is 0.5 to 3.

[20] The production method for a complex polyester composition according to [18] or [19], in which the step of performing the dehydration condensation includes a step of adding a hydrocarbon-based solvent having a boiling point of 110° C. to 160° C. in the amount of 1 mass % to 25 mass % with respect to the mixture, and of performing the dehydration condensation while setting water in an azeotropic state.

[21] The production method for a complex polyester composition according to [18] or [19], in which the step of performing the dehydration condensation is a step of performing condensation in the absence of a solvent.

According to the present invention, it is possible to obtain a complex polyester composition which is able to exhibit high lubrication performance even when under extreme pressure conditions. Further, when the complex polyester composition of the present invention is used, it is possible to obtain a lubricant having high transparency, and it is possible to easily determine the degree to which the deterioration of the lubricant has progressed or whether or not foreign substances are mixed into the lubricant. For this reason, the complex polyester composition of the present invention has excellent usability, and is preferably used as a lubricant in various applications.

DESCRIPTION OF THE PREFERRED EMBODIMENTS

Hereinafter, the present invention will be described in detail. The following description of configuration requirements are based on representative embodiments or specific examples, but the present invention is not limited to the embodiments. Furthermore, herein, "to" indicates a range including the numerical values before and after "to" as the lower limit value and the upper limit value.

(Complex Polyester Composition)

The present invention relates to a complex polyester composition containing predetermined polyester. The complex polyester composition of the present invention contains polyester which is obtained by condensing polyhydric alcohol having at least two hydroxyl groups, a dicarboxylic acid having 44 carbon atoms, and monohydric alcohol. In the present invention, it is possible to obtain a complex polyester composition which is able to exhibit high lubrication performance even when under extreme pressure conditions by containing such specific polyester. Further, the complex polyester composition obtained in the present invention has high transparency.

<Polyhydric Alcohol>

The polyhydric alcohol used in the condensation of the polyester is a compound having at least two hydroxyl groups. The polyhydric alcohol is denoted by $R(OH)_n$. R represents an n-valent aliphatic group, an n-valent aliphatic ring group, or an n-valent aromatic ring group, and in carbon atoms of R, one or more carbon atoms which are not adjacent to each other may be substituted with an oxygen atom. The number of hydroxyl groups included in one molecule of the polyhydric alcohol is preferably 2 to 6, and is more preferably 3 to 6.

Any one type of bivalent to hexavalent polyhydric alcohol may be used as the polyhydric alcohol used in the present invention, or a plurality of types of bivalent to hexavalent polyhydric alcohols may be used as the polyhydric alcohol used in the present invention. For example, among the bivalent to hexavalent polyhydric alcohols, any two types of bivalent to hexavalent polyhydric alcohols may be used by being mixed, any three types of bivalent to hexavalent polyhydric alcohols may be used by being mixed, or all of five types of bivalent to hexavalent polyhydric alcohols may be used by being mixed. Furthermore, when the polyhydric alcohol contains the bivalent polyhydric alcohol, a content ratio of the bivalent polyhydric alcohol is preferably less than or equal to 40 mass %, is more preferably less than or equal to 30 mass %, and is even more preferably less than or equal to 20 mass %, with respect to the total mass of the polyhydric alcohol.

R is an n-valent aliphatic group which preferably has 2 to 20 carbon atoms, more preferably has 2 to 15 carbon atoms, even more preferably has 2 to 10 carbon atoms, still more preferably has 2 to 7 carbon atoms, and particularly preferably has 3 to 6 carbon atoms. However, the present invention is not limited to this range, and it may be preferable that the number of carbon atoms increases according to the application.

It is more preferable that R represents a group denoted by $C_xH_{2x+2-n}$ (x represents a numerical value of 2 to 20) or $C_xH_{2x+2-n}O_m$ (x represents a numerical value of 2 to 20, m represents a numerical value satisfying m<x, and m≤x/2 is preferable).

Examples of the polyhydric alcohol which is able to be used in the present invention are able to include the following compounds. Examples of the polyhydric alcohol which is able to be used in the present invention include diol such as ethylene glycol, propylene glycol, 1,4-butane diol, 1,3-butane diol, 1,6-hexane diol, 1,4-dimethylol cyclohexane, and neopentyl glycol; triol such as trimethylol methane, trimethylol ethane, trimethylol propane, trimethylol butane, and glycerin; tetraol such as tetramethylol propane, maltiol such as dipentaerythritol and tripentaerythritol; sugar alcohol such as xylitol, sorbitol, mannitol, erythritol, maltitol, isomalt, arabinitol, ribitol, iditol, volemitol, and perseitol; sugar such as glucose; and the like. Among them, the neopentyl glycol, the trimethylol ethane, the trimethylol propane, the trimethylol butane, the glycerin, the pentaerythritol, the dipentaerythritol, and the xylitol are preferable; polyhydric alcohol having three of more hydroxyl groups, such as the trimethylol propane, the trimethylol butane, the glycerin, the pentaerythritol, and the dipentaerythritol is more preferable; the trimethylol propane, the glycerin, the pentaerythritol, the dipentaerythritol, and the like are even more preferable; and the pentaerythritol and the trimethylol propane are particularly preferable. It is not necessary that these polyhydric alcohols are high-purity products, and are preferably used in a so-called industrial grade. For example, the industrial grade of pentaerythritol is formed of mono-pentaerythritol of approximately 88%, di-pentaerythritol of 10%, and tri-pentaerythritol of 1% to 2%, and in the present invention, the industrial grade of the pentaerythritol or the like is able to be used as the polyhydric alcohol.

Hereinafter, specific examples of the polyhydric alcohol which is able to be used in the present invention will be described, but the present invention is not limited thereto.

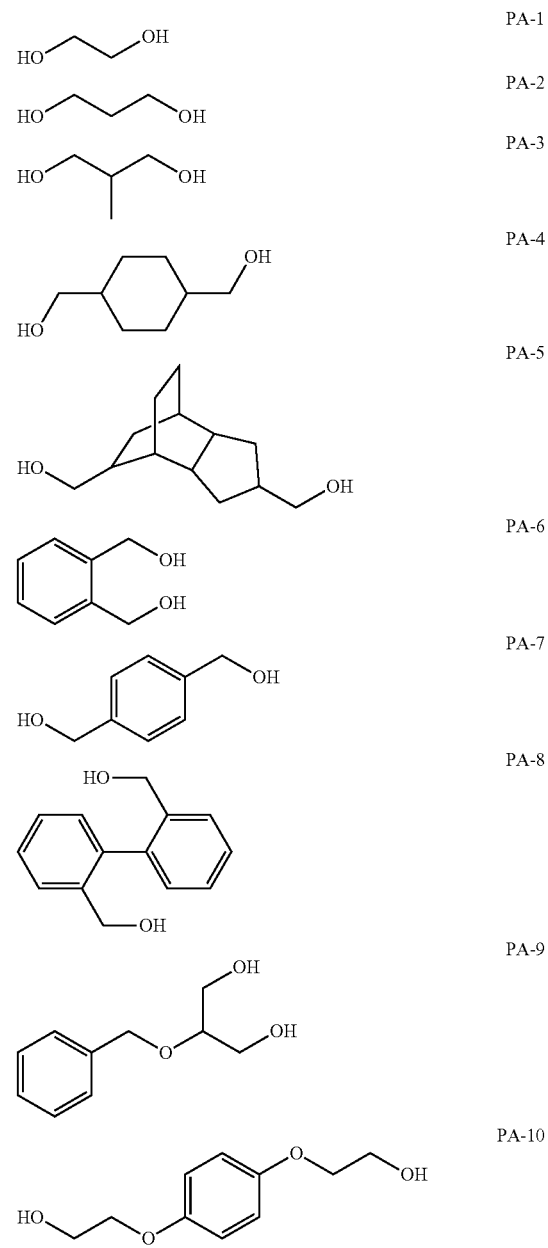

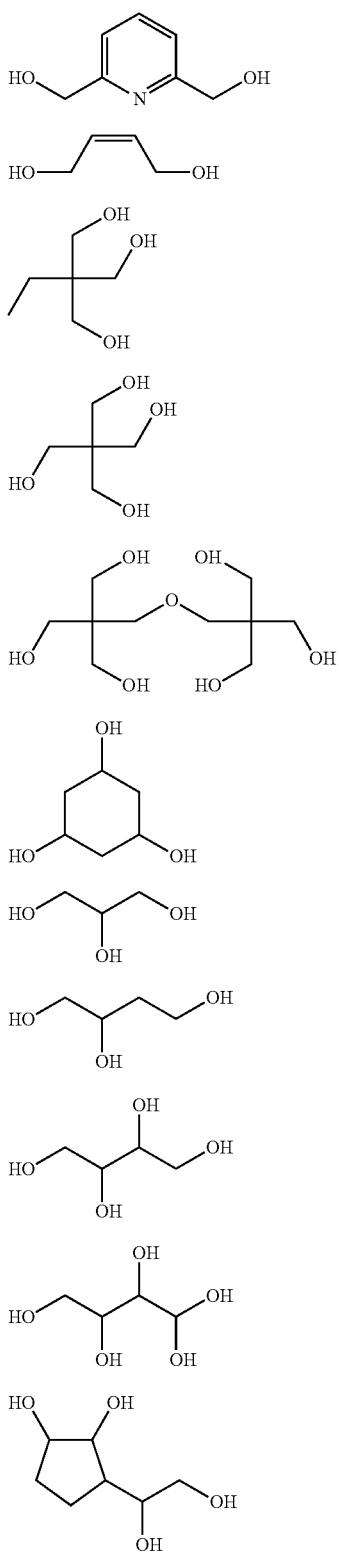

PA-11
PA-12
PA-13
PA-14
PA-15
PA-16
PA-17
PA-18
PA-19
PA-20
PA-21

<Dicarboxylic Acid Having 44 Carbon Atoms>

The dicarboxylic acid having 44 carbon atoms used in the condensation of the polyester is preferably a dimer of an unsaturated fatty acid having 22 carbon atoms, and is more preferably an erucic acid dimer. Here, the erucic acid dimer is a dicarboxylic acid having 44 carbon atoms in which an unsaturated fatty acid (an erucic acid) having 22 carbon atoms is dimerized. Examples of the erucic acid which is preferably used in dimerization of the erucic acid dimer are able to include a compound of CAS number 112-86-7 or the like. In addition, a representative erucic acid dimer is an erucic acid dimer of a product name of Pripol 1004 (manufactured by Croda International Plc) or the like.

<Monohydric Alcohol>

The monohydric alcohol used in the condensation of the polyester is a compound having one hydroxyl group in one molecule. The monohydric alcohol is denoted by R(OH). R represents a monovalent aliphatic group, a monovalent aliphatic ring group, or a monovalent aromatic ring group, and in carbon atoms of R, one or more carbon atoms which are not adjacent to each other may be substituted with an oxygen atom. The number of carbon atoms of R is preferably greater than or equal to 4, is more preferably greater than or equal to 6, and is even more preferably greater than or equal to 8. By setting the number of carbon atoms of the monohydric alcohol to be in the range described above, it is possible to suppress volatilization of the monohydric alcohol at the time of performing a condensation reaction, and it is possible to efficiently perform the condensation reaction of the polyester.

Examples of the monohydric alcohol which is suitable for the present invention include butanol, pentanol, propanol, hexanol, heptanol, octanol, decanol, dodecanol, hexadecanol, octadecanol, eicosadecanol, phytosterol, isostearol, stearol, cetol, behenol, ethylene glycol monoether, polyethylene glycol monoether, and the like.

Hereinafter, specific examples of the monohydric alcohol which is able to be used in the present invention will be described, but the present invention is not limited thereto.

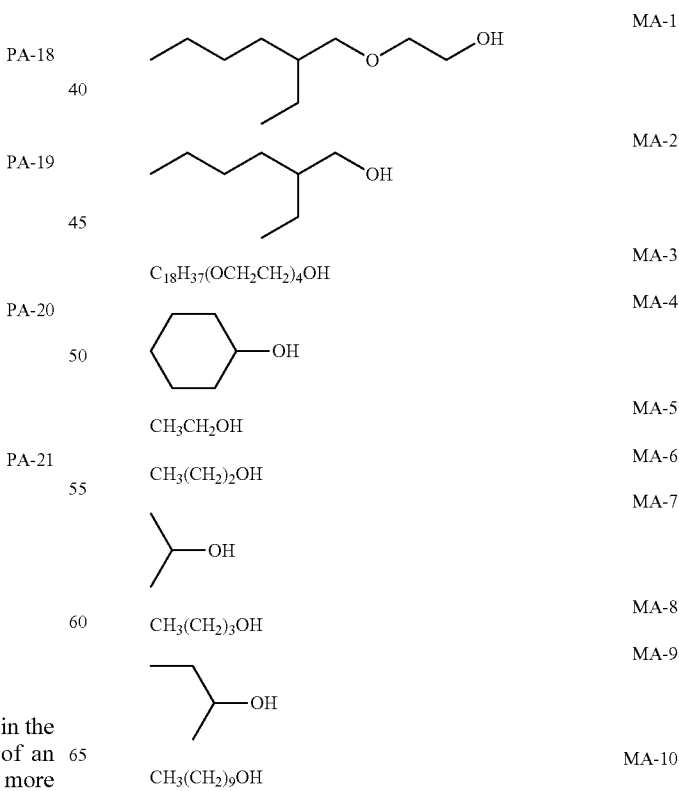

-continued

CH₃(CH₂)₁₁OH

CH₃(CH₂)₁₃OH

CH₃(CH₂)₁₅OH

CH₃(CH₂)₁₇OH

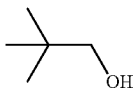

CH₃(OC₂H₄)₂OH

C₂H₅(OC₂H₄)₃OH

C₄H₉(OC₃H₆)₃OH

CH₃(OC₂H₄)₆OH

C₂H₅(OC₄H₈)₅OH

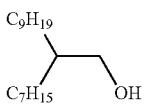

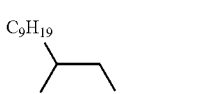

(CH₃)₃Si(OSi(CH₃)₂)₄(OC₂H₄)₄OH

C₆F₁₃CH₂CH₂OH

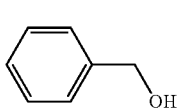

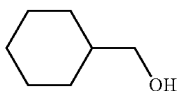

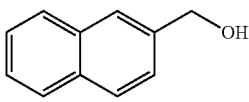

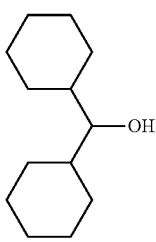

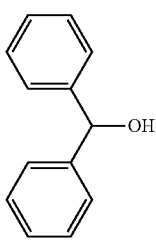

MA-11

MA-12

MA-13

MA-14

MA-15

MA-16

MA-17

MA-18

MA-19

MA-20

MA-21

MA-22

MA-23

MA-24

MA-25

MA-26

MA-27

MA-28

MA-29

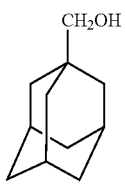

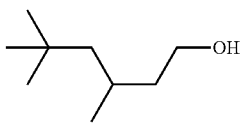

CH₃OH

MA-30

MA-31

MA-32

It is preferable that the monohydric alcohol used in the present invention is denoted by General Formula (1) described below.

$$R^a\text{-}(O(CX^{a1}X^{a2})^{na1})_{na2}OH \qquad \text{General Formula (1)}$$

Here, in General Formula (1), $R^a$ represents an alkyl group which may have a substituent group, a cycloalkyl group which may have a substituent group, an alkenyl group which may have a substituent group, an aryl group which may have a substituent group, or a heteroaryl group which may have a substituent group, and $X^{a1}$ and $X^{a2}$ each independently represent a hydrogen atom, a halogen atom, or an alkyl group. In addition, na1 represents an integer of 2 to 4, and na2 represents an integer of 1 to 12.

In an alkyl group portion of the alkyl group represented by $R^a$ which may have a substituent group, the number of carbon atoms is preferably 3 to 22, is more preferably 4 to 17, and is even more preferably 5 to 13. The alkyl group represented by $R^a$ may be a straight-chain alkyl group or a branched alkyl group. In addition, $R^a$ may be a cycloalkyl group.

In an alkenyl group portion of the alkenyl group represented by $R^a$ which may have a substituent group, the number of carbon atoms is preferably 3 to 17, is more preferably 4 to 13, and is even more preferably 5 to 9. The alkenyl group represented by $R^a$ may be a straight-chain alkyl group, a branched alkyl group, or a cyclic alkyl group.

In an aryl group portion of the aryl group or the heteroaryl group represented by $R^a$ which may have a substituent group, the number of carbon atoms is preferably 6 to 17, and is more preferably 6 to 12. Examples of the aryl group represented by $R^a$ are able to include a phenyl group, a naphthyl group, and the like, and among them, the phenyl group is particularly preferable. In addition, an imidazolyl group, a pyridyl group, a quinolyl group, a furyl group, a thienyl group, a benzoxazolyl group, an indolyl group, a benzimidazolyl group, a benzothiazolyl group, a carbazolyl group, and an azepinyl group are able to be exemplified as the heteroaryl group represented by $R^a$. An oxygen atom, a sulfur atom, and a nitrogen atom are preferable as a hetero atom contained in the heteroaryl group, and among them, the oxygen atom is preferable.

Among them, in General Formula (1), it is preferable that $R^a$ is the alkyl group which may have a substituent group. Here, the alkyl group may be an alkyl group having a branch. In addition, it is more preferable that $X^{a1}$ and $X^{a2}$ each independently is a hydrogen atom or an alkyl group.

In General Formula (1), na1 is preferably an integer of 2 or 3, and is more preferably an integer of 2. In addition, na2 is preferably an integer of 1 to 8, is more preferably an integer of 1 to 6, and is particularly preferably an integer of 1 to 3.

The number of carbon atoms of the monohydric alcohol denoted by General Formula (1) is preferably greater than or equal to 4, is more preferably greater than or equal to 6, and is even more preferably greater than or equal to 8. By using such monohydric alcohol, it is possible to suppress the volatilization of the monohydric alcohol at the time of performing the condensation reaction, and it is possible to efficiently perform the condensation reaction of the polyester.

Examples of the substituent group which is able be included in $R^a$ include a substituted or unsubstituted alkyl group having 1 to 50 carbon atoms (for example, methyl, ethyl, straight-chain or branched-chain propyl, straight-chain or branched-chain butyl, straight-chain or branched-chain pentyl, straight-chain or branched-chain hexyl, straight-chain or branched-chain heptyl, straight-chain or branched-chain octyl, straight-chain or branched-chain nonyl, straight-chain or branched-chain decyl, straight-chain or branched-chain undecyl, straight-chain or branched-chain dodecyl, straight-chain or branched-chain tridecyl, straight-chain or branched-chain tetradecyl, straight-chain or branched-chain pentadecyl, straight-chain or branched-chain hexadecyl, straight-chain or branched-chain heptadecyl, straight-chain or branched-chain octadecyl, straight-chain or branched-chain nonadecyl, straight-chain or branched-chain eicosyl, straight-chain or branched-chain heneicosyl, straight-chain or branched-chain docosyl, straight-chain or branched-chain tricosyl, or straight-chain or branched-chain tetracosyl); an alkenyl group having 2 to 35 carbon atoms (for example, propenyl, butenyl, pentenyl, hexenyl, heptenyl, octenyl, nonenyl, decenyl, undecenyl, and dodecenyl); a cycloalkyl group having 3 to 10 carbon atoms (for example, cyclopropyl, cyclobutyl, cyclopentyl, cyclohexyl, and cycloheptyl); an aromatic ring group having 6 to 30 carbon atoms (for example, phenyl, naphthyl, biphenyl, phenanthryl, and anthracenyl), a hetero ring group (preferably a residue of a hetero ring containing at least one hetero atom selected from a nitrogen atom, an oxygen atom, and a sulfur atom, and for example, pyridyl, pyrimidyl, triazinyl, thienyl, furyl, pyrrolyl, pyrazolyl, imidazolyl, triazolyl, thiazolyl, oxazolyl, thiadiallyl, oxadiazolyl, quinolyl, and isoquinolyl); or a group formed of a combination thereof. The substituent group may have one or more substituent groups when it is possible, and examples of the substituent group include an alkoxy group, an alkoxy carbonyl group, a halogen atom, an ether group, an alkyl carbonyl group, a cyano group, a thioether group, a sulfoxide group, a sulfonyl group, an amide group, and the like.

(Other Compound)

In order to obtain the polyester of the present invention, for example, the condensation may be performed by further mixing a dimer acid in addition to the polyhydric alcohol, the dicarboxylic acid having 44 carbon atoms, and the monohydric alcohol. In the present invention, the dicarboxylic acid having 44 carbon atoms and the dimer acid may be used together, or the erucic acid dimer and the dimer acid may be used together. A mixing ratio of the dicarboxylic acid having 44 carbon atoms and the dimer acid is preferably 1:0.1 to 4, is more preferably 1:0.2 to 2, and is even more preferably 1:0.5 to 1.

Further, in the present invention, for example, the condensation may be performed by further mixing a trimer acid in addition to the polyhydric alcohol, the dicarboxylic acid having 44 carbon atoms, and the monohydric alcohol. That is, in the present invention, dicarboxylic acid having 44 carbon atoms and the trimer acid may be used together, or the erucic acid dimer and the trimer acid may be used together. Furthermore, both of the dimer acid and the trimer acid are able to be mixed in addition to the dicarboxylic acid having 44 carbon atoms. A mixing ratio of the dicarboxylic acid having 44 carbon atoms and the trimer acid is preferably 1:0.05 to 2, is more preferably 1:0.1 to 1, and is even more preferably 1:0.2 to 0.5.

Here, the dimer acid indicates an aliphatic dicarboxylic acid or an alicyclic dicarboxylic acid (in general, a trimer, a monomer, and the like are contained in several mol % in addition to a dimer which is the majority of the contents) which is generated by dimerizing an unsaturated fatty acid (in general, an unsaturated fatty acid having 18 carbon atoms) by polymerization, Diels-Alder reaction, or the like, and among them, an aliphatic dicarboxylic acid or an alicyclic dicarboxylic acid containing a trimer as a main component is defined as the trimer acid. In specific examples of the dimer acid or the trimer acid, Tsunodymes (Registered Trademark) 205, 216, 228, and 395 manufactured by TSUNO CO., LTD. are exemplified as the dimer acid, and Tsunodyme 345 or the like is exemplified as the trimer acid.

In addition, in the present invention, other components may be used in the condensation reaction in addition to the polyhydric alcohol, the dicarboxylic acid having 44 carbon atoms, and the monohydric alcohol, and the complex polyester composition containing the polyester to be obtained is preferably used.

(Polyester)

The complex polyester composition of the present invention contains the polyester which is obtained by mixing the polyhydric alcohol, the dicarboxylic acid having 44 carbon atoms, and the monohydric alcohol as described above, and by condensing the mixture. It is preferable that at least one type of polyester obtained by condensing the mixture is denoted by General Formula (2) described below.

$$R(\text{—OCOR}^1\text{COOR}^2)_n \qquad \text{General Formula (2)}$$

Here, in General Formula (2), R represents a n-valent atomic group, $R^1$ represents a residue of the dicarboxylic acid having 44 carbon atoms, and $R^2$ represents an alkyl group which may have a substituent group, a cycloalkyl group which may have a substituent group, an alkenyl group which may have a substituent group, an aryl group which may have a substituent group, or a heteroaryl group which may have a substituent group. In addition, n represents an integer of 2 to 6.

In General Formula (2) described above, R represents a bivalent to hexavalent atomic group. In General Formula (2), it is preferable that n is an integer of 3 to 6, and it is preferable that R is a trivalent to hexavalent atomic group. That is, it is preferable that the polyhydric alcohol having at least two hydroxyl groups is a compound having three or more hydroxyl groups.

Furthermore, the structure of the polyester when R is a trivalent atomic group is able to be denoted by General Formula (3), and the structure of the polyester when R is a tetravalent atomic group is able to be denoted by General Formula (4).

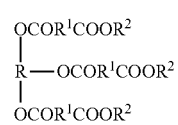

General Formula (3)

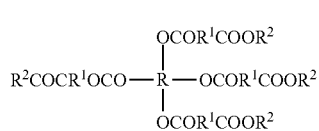

General Formula (4)

In General Formula (3), R represents a trivalent atomic group, and $R^1$ and $R^2$ are identical to $R^1$ and $R^2$ in General Formula (2). In addition, in General Formula (4), R represents a tetravalent atomic group, and $R^1$ and $R^2$ are identical to $R^1$ and $R^2$ in General Formula (2).

In General Formulas (2) to (4), the number of carbon atoms of R is preferably 2 to 20, is more preferably 2 to 15, is even more preferably 2 to 10, is still more preferably 2 to 7, and is particularly preferably 3 to 6.

It is preferable that an atom configuring an atomic group R is a carbon atom, a hydrogen atom, and an oxygen atom. It is preferable that R is an aliphatic hydrocarbon atomic group which may have a substituent group or an aromatic hydrocarbon atomic group which may have a substituent group. Among them, it is particularly preferable that R is an atomic group formed of saturated aliphatic hydrocarbon which may have a substituent group. According to the configuration of R described above, it is possible to obtain a complex polyester composition having excellent lubrication performance.

$R^1$ represents the residue of the dicarboxylic acid having 44 carbon atoms. Here, the residue of the dicarboxylic acid having 44 carbon atoms indicates a group configuring a portion excluding two carboxyl groups from the dicarboxylic acid having 44 carbon atoms.

$R^2$ represents an alkyl group which may have a substituent group, a cycloalkyl group which may have a substituent group, an alkenyl group which may have a substituent group, an aryl group which may have a substituent group, and a heteroaryl group which may have a substituent group. In General Formula (1), groups represented by $R^a$ are able to be exemplified as a specific group which is able to be included in $R^2$. Furthermore, a substituent group of each group which is able to be included in $R^2$ is not particularly limited. The same substituent groups as described above are able to be exemplified as the substituent group.

The number of carbon atoms of $R^2$ is preferably greater than or equal to 4, is more preferably greater than or equal to 6, and is even more preferably greater than or equal to 8.

In addition, it is preferable that $R^2$ is a group having an oxyalkylene structure. That is, it is preferable that $R^2$ is a branched alkyl group or an alkyl group having an ether bond in a chain. By setting $R^2$ to be such a substituent group, it is possible to further increase the lubrication performance of the complex polyester composition.

When the compound of the polyhydric alcohol, the dicarboxylic acid having 44 carbon atoms, and the monohydric alcohol are mixed, it is preferable that the equivalence ratio of mixing the dicarboxylic acid having 44 carbon atoms with respect to the polyhydric alcohol is 1 to 3, and an equivalence ratio of mixing the monohydric alcohol with respect to the polyhydric alcohol is 0.5 to 3. That is, it is preferable that the mixing ratio is Polyhydric Alcohol:Dicarboxylic Acid Having 44 Carbon Atoms:Monohydric Alcohol=1:1 to 3:0.5 to 3. The mixing ratio is more preferably 1:1.2 to 2.8:0.7 to 2.8, and is even more preferably 1:1.5 to 2.5:1 to 2.5. In particular, it is preferable that a side chain of the polyester is end capped, and thus it is preferable that the total equivalent weights of the polyhydric alcohol and the monohydric alcohol are greater than or equal to the equivalent weight of the dicarboxylic acid having 44 carbon atoms.

It is preferable that the viscosity of the complex polyester composition of the present invention at 40° C. is 50 mPa·s to 1650 mPa·s. The viscosity of the complex polyester composition at 40° C. is preferably greater than or equal to 50 mPa·s, is more preferably greater than or equal to 70 mPa·s, and is even more preferably greater than or equal to 100 mPa·s. In addition, the viscosity of the complex polyester composition at 40° C. is preferably less than or equal to 1650 mPa·s, is more preferably less than or equal to 1200 mPa·s, and is even more preferably less than or equal to 1000 mPa·s. By setting the viscosity of the complex polyester composition to be in the range described above, it is possible to suppress a friction coefficient of the complex polyester composition to be low, and thus it is possible to increase the lubrication performance.

The complex polyester composition of the present invention has the configuration as described above, and thus has excellent characteristics such as a small increase in the friction coefficient from general fluid lubrication or an elastic fluid lubrication region to an extreme pressure region. It is considered that such an excellent effect is obtained by having a stereoscopic structure of the polyester obtained in the present invention in which side chains are radially arranged. The polyester obtained in the present invention is a compound configured of the polyhydric alcohol which is able to radially arrange the side chains, the dicarboxylic acid having 44 carbon atoms which is connected to the polyhydric alcohol and is radially stretched, and the monohydric alcohol which is a terminal linking group of the dicarboxylic acid having 44 carbon atoms. In the present invention, the polyester has the side chain by using the polyhydric alcohol as a center atomic group, and thus it is possible to ensure a large free volume by the stereoscopic structure. Accordingly, it is possible to suppress an increase in the viscosity and the friction coefficient of the compound even when under high pressure.

In the present invention, a light component may be further included in addition to the predetermined polyester. Here, the light component indicates a component having a low molecular weight, and indicates ester obtained by a reaction between all carboxyl groups of the dicarboxylic acid having 44 carbon atoms and the monohydric alcohol and ester having a molecular weight which is smaller than that of the ester described above. By allowing a liquid having low viscosity, such as the light component, to further coexist, it is possible to further decrease the viscosity of the complex polyester composition. Accordingly, it is possible to exhibit high lubrication performance even when under extreme pressure conditions.

In the complex polyester composition of the present invention, a ratio of the predetermined polyester and the light component is not particularly limited. In an aspect where the complex polyester composition is used for a lubricant, a content ratio of the light component is preferably less than or equal to 50 mass %, is more preferably less than or equal to 45 mass %, and is even more preferably less than or equal to 40 mass %, with respect to the predetermined polyester. Furthermore, the lower limit value is not particularly limited, but is preferably greater than or equal to 15 mass %.

In a production method described below, the ratio of the predetermined polyester and the light component is able to be attained by being controlled with a feed ratio of three raw materials. In addition, the ratio of the predetermined polyester and the light component is able to be adjusted to be in a preferred range by separating the light component by distillation or the like, and by mixing the light component with remaining polyester at an arbitrary ratio.

Furthermore, a composition ratio of the predetermined polyester and the light component containing dimer diol is able to be calculated by performing measurement of gel permeation chromatography (GPC). The light component has a sharp peak and strong intensity in GPC analysis, and thus is easily discriminated.

In the present invention, unreacted COOH in the dicarboxylic acid having 44 carbon atoms may remain in the side chain of the polyester contained in the complex polyester composition, and unreacted OH in the polyhydric alcohol or the monohydric alcohol may remain in the side chain, and when OH and COOH remain in the side chain, a hydroxyl value and an acid value increases, and thus OH and COOH remaining in the side chain may not be preferable according to the application (for example, the application of a lubricant, and the like). In such a case, OH and COOH in the polyester are eliminated by a separate acylation treatment and/or an esterification treatment, and thus the hydroxyl value and the acid value are able to be reduced.

In order to eliminate OH in the polyester, polyester in which OH remains in a side chain is obtained, and then a treatment is able to be performed in which at least a part of the polyester is acylated. The acylation treatment is a treatment in which a monobasic acid ($R^1COOH$) or a monobasic acid anhydride (($R^1CO)_2O$) is added to the polyester having OH remaining therein and is heated, and thus remaining OH is converted into $OCOR^1$. It is preferable that the hydroxyl value is reduced by the acylation treatment from a viewpoint of easy mixing properties of the polyester at the time of being mixed with other oily mediums.

In addition, a treatment of eliminating COOH in polyester may be performed. For example, esterification is able to be performed by treating the polyester with diazomethane or the like.

A ratio of unreacted OH in the polyester is determined by measuring $^{13}C$-NMR. In the application of a lubricant, a residual ratio of OH in the polyester is preferably 0% to 40%, is more preferably 0% to 35%, and is even more preferably 0% to 30%. In addition, in the application of a lubricant, the acid value of the polyester (the number of mg of KOH required for neutralizing 1 g of a sample) is preferably 0 to 50, is more preferably 0 to 40, and is even more preferably 0 to 30. However, the present invention is not limited to the range described above.

(Production Method of Complex Polyester Composition)

The complex polyester composition of the present invention is able to be obtained by feeding at least three raw materials of the polyhydric alcohol, the dicarboxylic acid having 44 carbon atoms, and the monohydric alcohol described above, and by performing dehydration condensation. That is, a production method of the complex polyester composition of the present invention includes a step of obtaining a mixture by mixing polyhydric alcohol having at least two hydroxyl groups, a dicarboxylic acid having 44 carbon atoms, and monohydric alcohol, and a step of performing dehydration condensation with respect to the mixture. Furthermore, in a producing step, two raw materials (for example, polyhydric alcohol and a dicarboxylic acid having 44 carbon atoms, or a dicarboxylic acid having 44 carbon atoms and monohydric alcohol) may react with each other in advance, and then the remaining raw material may react with the reacted raw materials.

A feed ratio (a mixing ratio) of the polyhydric alcohol, the dicarboxylic acid having 44 carbon atoms, and the monohydric alcohol is determined by an equivalent weight. Here, the equivalent weight indicates a chemical equivalent weight of COOH or OH in a reaction. When the number of OH groups in one molecule of the polyhydric alcohol is n, and the number of moles is M1, the equivalent weight of the polyhydric alcohol is defined by n×M1. Similarly, the number of COOH groups in one molecule of the dicarboxylic acid having 44 carbon atoms is 2, and thus when the number of moles is M2, the equivalent weight of the dicarboxylic acid having 44 carbon atoms is defined by 2×M2. The number of OH groups in one molecule of the monohydric alcohol is 1, and thus when the number of moles is M3, the equivalent weight of the monohydric alcohol is defined by M3. The ratio described above is a ratio of n×M1, 2×M2, and M3.

In the present invention, it is preferable that the mixing ratio is Polyhydric Alcohol:Dicarboxylic Acid Having 44 Carbon Atoms:Monohydric Alcohol=1:1 to 3:0.5 to 3. The mixing ratio is more preferably 1:1.2 to 2.8:0.7 to 2.8, and is even more preferably 1:1.5 to 2.5:1 to 2.5. In particular, it is preferable that the side chain of the polyester is end capped, and thus it is preferable that the total equivalent weights of the polyhydric alcohol and the monohydric alcohol are greater than or equal to the equivalent weight of the dicarboxylic acid having 44 carbon atoms.

The mixture fed as described above is subjected to a dehydration condensation reaction in the presence of a catalyst or in the absence of a catalyst, and thus it is possible to obtain the complex polyester composition of the present invention.

In the dehydration condensation, it is preferable that heating is performed or a suitable amount of azeotropic solvent with water is present. Accordingly, a product is not colored, and the dehydration smoothly progresses. The solvent is preferably a hydrocarbon-based solvent having a boiling point of 100° C. to 200° C., is more preferably a hydrocarbon-based solvent having a boiling point of 100° C. to 170° C., and is most preferably a hydrocarbon-based solvent having a boiling point of 110° C. to 160° C. Examples of the solvent include toluene, xylene, mesitylene, and the like. When the added amount of the solvent excessively increases, a liquid temperature is in the vicinity of the temperature of the solvent, and thus the dehydration condensation rarely progresses. In contrast, when added amount of the solvent excessively decreases, azeotropy is not smoothly performed. Therefore, the added amount is preferably 1 mass % to 25 mass %, is more preferably 2 mass % to 20 mass %, is particularly preferably 3 mass % to 15 mass %, and is also preferably 5 mass % to 12 mass %, with respect to the total amount of the polyhydric alcohol, the dicarboxylic acid having 44 carbon atoms, and the monohydric alcohol.

The reaction is accelerated by using the catalyst, but a post treatment of removing the catalyst is complex, and causes coloration of a product, and thus it is preferable that the catalyst is not used. However, when the catalyst is used, general conditions and operations are used in general catalysts. In reference to this, it is possible to refer to the references disclosed in JP2001-501989A, JP2001-500549A, JP2001-507334A, and JP2002-509563A.

In addition, in the present invention, the mixture may be condensed in the absence of a solvent. Here, conditions of "in the absence of a solvent" indicates that a content ratio of the solvent is less than or equal to 1 mass % with respect to the total amount of the polyhydric alcohol, the dicarboxylic acid having 44 carbon atoms, and the monohydric alcohol, and containing a small amount of solvent of less than or equal to 1 mass % is included in the conditions of "in the absence of a solvent" in the present invention.

The reaction is performed after the feeding at a liquid temperature of 120° C. to 250° C., preferably 130° C. to 240° C., more preferably 130° C. to 230° C., and particularly preferably 140° C. to 220° C. Accordingly, the solvent containing water is in an azeotropic state, is cooled in a cooling portion such as Dean-Stark, and becomes a liquid, and thus water and the solvent are separated from each other. The water may be removed.

In a reaction time, a theoretical amount of generated water is calculated from the number of moles of the fed materials, and thus it is preferable that the reaction is performed until the theoretical amount of generated water is obtained, but it is difficult to completely perform the reaction in this manner. Even when the reaction is performed until the theoretical amount of generated water is 60% to 90%, the complex polyester composition has excellent lubrication properties. The reaction time is 1 hour to 24 hours, is preferably 3 hours to 18 hours, is more preferably 5 hours to 18 hours, and is most preferably 6 hours to 15 hours.

After the dehydration condensation is performed and a volatile component is removed, remaining OH may be further acylated. When the acylation is performed, a suitable amount of monobasic acid ($R^1COOH$) or monobasic acid anhydride ($(R^1CO)_2O$), and preferably monobasic acid anhydride ($(R^1CO)_2O$), is added and is heated to a temperature of preferably higher than or equal to 100° C., more preferably higher than or equal to 120° C., and particularly preferably higher than or equal to 150° C., and thus at least a part of remaining OH, and preferably almost all of remaining OH, is able to be converted to $OCOR^1$. It is preferable that the volatile component which is by-produced is removed by distillation described below. Furthermore, $R^1$ is an alkyl group or an aryl group having 1 to 10 carbon atoms, is more preferably an alkyl group or an aryl group having 1 to 6 carbon atoms, and is even more preferably a methyl group, an ethyl group, a butyl group, and a phenyl group, and among them, the methyl group or the phenyl group is preferable, and the methyl group is particularly preferable.

In addition, in order to eliminate remaining COOH, an esterification treatment may be performed after the dehydration condensation is performed and the volatile component is removed. The esterification treatment, for example, is able to be performed by adding diazomethane, and at least a part of COOH, and preferably almost all of COOH, is able to be converted into methyl ester.

According to this reaction, it is possible to obtain a complex polyester composition which contains the predetermined polyester, and a light component containing at least ester generated as described above. After the dehydration condensation reaction is performed, as necessary, the acylation treatment and/or the esterification treatment are performed, and then the obtained complex polyester composition is able to be directly used in various applications, for example, as a lubricant. In addition, according to the application, various treatments may be performed.

It is preferable that filtration is performed after the reaction and the treatment after the reactions are performed, and thus waste and the like are removed. Furthermore, when complex polyester is a solid, it is possible to obtain the complex polyester composition by melting the solid complex polyester or by reprecipitating the solid complex polyester as a powder.

(Lubricant Composition)

The present invention may relate to a lubricant composition containing at least the complex polyester composition. For example, the complex polyester composition of the present invention, along with various additives and/or mediums, is able to be added to the lubricant composition.

Examples of the additive are able to include one type or two or more types of additives selected from an abrasion preventing agent, a viscosity index improver, an antioxidant, a cleaning agent, a dispersant, a fluidizing agent, a curing agent, a corrosion preventing agent, a seal compatible agent, a defoaming agent, a rust preventing agent, a friction adjuster, and a thickener.

By adding such an additive, a preferred function as a lubricant, such as suppression in abrasion, is able to be imparted to the lubricant composition. Lubricants which are able to be used in the present invention are able to refer to the description in paragraphs "0098" to "0165" of JP2011-89106A.

In addition, examples of the medium are able to include one type or two or more types of mediums selected from mineral oil, a fatty oil compound, polyolefin oil, silicone oil, ether oil (preferably perfluoropolyether oil and diphenyl ether oil), and ester oil (preferably aromatic ester oil, aliphatic monoester oil, aliphatic diester oil, and polyol ester lubricating oil).

In the present invention, the "medium" indicates all mediums generally referred to as a "flowable liquid". However, it is not necessary that the medium is in a liquid state at room temperature or at a temperature to be used, and a material in any state of a solid, a gel, and the like in addition to the liquid is able to be used. The medium used in the present invention is not particularly limited, but is able to be selected from various liquids according to the application. The mediums which are able to be used in the present invention are able to refer to the description in paragraphs "0067" to "0096" of JP2011-89106A.

(Properties of Lubricant Composition)

The viscosity of the lubricant composition of the present invention at 40° C. is preferably less than or equal to 1650 mPa·s, is more preferably less than or equal to 1200 mPa·s, and is even more preferably less than or equal to 1000 mPa·s. Suitable viscosity is obtained according to a use environment, and thus it is necessary that the viscosity is matched to the use environment.

The constituent elements of the lubricant composition of the present invention are preferably configured only of carbon, hydrogen, oxygen, and nitrogen, and are more preferably configured only of carbon, hydrogen, and oxygen. In addition, oil used as an oily medium has various materials configured only of carbon, hydrogen, and oxygen. By combining these materials, it is possible to prepare a composition in which the constituent elements are configured only of carbon, hydrogen, oxygen, and nitrogen.

Furthermore, current lubricating oil generally contains phosphorus, sulfur, and heavy metal. Lubricating oil used in a two-stroke engine in which the lubricating oil is combusted along with the fuel does not contain phosphorus and heavy metal in consideration of an environmental load, but sulfur is present in lubricating oil used in a four-stroke engine in the amount of approximately half of the lubricating oil. That is, in a current lubrication technology, it is assumed that it is essential to form a boundary lubrication film by using the least amount of sulfur, but a load on a catalyst for purifying exhaust gas is extremely considerable by containing a sulfur element. In the catalyst for purifying the exhaust gas, platinum or nickel is used, but a poisoning function of phosphorus or sulfur becomes a significant problem. From this viewpoint, it is extremely advantageous that the elements configuring the composition of the lubricating oil are configured only of carbon, hydrogen, oxygen, and nitrogen. Further, the lubricating oil configured only of carbon, hydrogen and oxygen is optimized for lubricating oil of an industrial machine, in particular, an associated apparatus for processing food, other than the engine oil. In the current technology, an element composition is used in which friction coefficient is sacrificed in consideration of the environment. This is a technology which is extremely preferable, even in lubricating oil for machining and working metal which require a large amount of water for cooling.

(Preparation Method of Lubricant Composition)

The lubricant composition of the present invention is able to be prepared by adding the complex polyester composition into an oily medium or an aqueous medium, and by dissolving and/or dispersing the complex polyester composition therein. The dissolving and/or dispersing may be performed in under heating. It is preferable that the added amount of the complex polyester composition is greater than or equal to 10 mass % with respect to the mass of the oily medium. However, the present invention is not limited to the range described above, and the compound described above may not be in the range described above insofar as the amount of the complex polyester composition is sufficient for exhibiting a friction reducing function.

(Application of Lubricant Composition)

The lubricant composition of the present invention is useful as a lubricant. That is, the present invention relates to a lubricant containing the complex polyester composition described above or a lubricant containing the lubricant composition described above.

The lubricant of the present invention, for example, is supplied between two sliding surfaces, and thus is able to be used for reducing friction. The composition of the present invention is able to form a film on the sliding surface. The material of the sliding surface is iron steel, and specifically, examples of the material of the sliding surface include carbon steel for a structure machine use, alloy steel for a structure machine use such as a nickel chromium steel material, a nickel chromium molybdenum steel material, a chromium steel material, a chromium molybdenum steel material, and an aluminum chromium molybdenum steel material, stainless steel, maraging steel, and the like.

Various metals other than iron steel, or an inorganic material or an organic material other than metal are widely used as the material of the sliding surface. Examples of the inorganic material or the organic material other than metal include various plastics, ceramics, carbons, and mixtures thereof. More specifically, examples of a metal material other than iron steel include cast iron, a copper-copper-lead-aluminum alloy, and cast metal and white metal thereof.

Furthermore, the materials of the sliding surface are able to refer to the description in paragraphs "0168" to "0175" of JP2011-89106A, The lubricant of the present invention is able to be used in various applications. For example, the lubricant of the present invention is able to be used as lubricating oil for grease, a releasing agent, engine oil for an internal combustion engine, oil for metal working (machining), oil for a bearing, fuel for a combustion engine, vehicle engine oil, gear oil, operating oil for an automobile, lubricating oil for a vessel and an aircraft, machine oil, turbine oil, hydraulic operating oil, compressor and vacuum pump oil, freezer oil, lubricating oil for metal working, a lubricant for magnetic recording medium, a lubricant for a micro machine, a lubricant for an artificial bone, shock absorber oil, or rolling oil. Further, the lubricant of the present invention is also used in an air conditioner or a refrigerator including a reciprocating type or rotating type airtight compressor, an air conditioner or a dehumidifier for an automobile, a cooling device such as a freezer, a freezing refrigerating warehouse, a vending machine, a showcase, a chemical plant, and the like.

The lubricant of the present invention is useful as lubricating oil for metal working which does not contain a chlorine-based compound, for example, when a metal material such as an iron and steel material or an Al alloy is subjected to hot rolling, or is subjected to working such as machining, and is useful as metal working oil or metal plastic working oil such as cold rolling oil, machining oil, grinding oil, drawing oil, and press working oil of aluminum, and in particular, is useful as an inhibitor against abrasion, damage, and surface roughness at the time of performing high-speed and high-load working, and is useful as a metal working oil composition which is able to be applied to low-speed heavy machining such as broach working and gun drill working.

In addition, the lubricant of the present invention is able to be used in various lubricating oils for grease, a lubricant for magnetic recording medium, a lubricant for a micro machine, a lubricant for an artificial bone, and the like. In addition, it is possible to configure the element composition of the lubricant composition as a carbohydrate, and thus, for example, a composition in which sorbitan fatty acid ester containing polyoxy ethylene ether which is widely used in cake mix, salad dressing, shortening oil, chocolate, and the like as an emulsifier, a dispersant, and a solubilizer is used as base oil of edible oil is configured as lubricating oil, and therefore, high-performance lubricating oil which is entirely harmless to a human body is able to be used in the lubrication of a manufacturing device in a food manufacturing line or a medical instrument member or.

Further, the composition of the present invention is dispersed by being emulsified in water system or is dispersed in a polar solvent or a resin medium, and thus is able to be used as machining oil or rolling oil.

In addition, the lubricant composition of the present invention is able to be used as a releasing agent in various applications. For example, the lubricant composition of the present invention is used as a releasing agent of a polycarbonate resin, a flame retardant polycarbonate resin, a crystalline polyester resin which is a main component of a toner for forming an image used in an electrophotographic device, an electrostatic recording device, and the like, a thermoplastic resin composition for various moldings, an epoxy resin composition for sealing a semiconductor, and the like. In one aspect of the releasing agent, the content of the complex polyester composition is 0.01 parts by mass to 10 parts by mass (preferably 0.1 parts by mass to 5 parts by mass) with respect to 100 parts by mass of a resin such as a polycarbonate resin.

In addition, the lubricant of the present invention is kneaded into or is applied onto a fiber product of a clothing material or the like in advance, and thus is able to be used as a stain-proofing agent which accelerates removal of stain attached onto the fiber product and prevents the fiber product from being stained.

EXAMPLES

Hereinafter, the present invention will be more specifically described with reference to examples. Materials, used amounts, ratios, treatment contents, treatment sequences, and the like of the following examples are able to be suitably changed unless the changes cause deviance from the gist of the present invention. Accordingly, the range of the present invention will not be limited to the following specific examples.

Examples 1 to 42

<Synthesis of Polyester>

Polyhydric alcohol, an erucic acid dimer, a dimer acid, and monohydric alcohol shown in Table 1 were put into a reaction vessel which was attached with a Dean-Stark dehydration device such that the amount of each material was as shown in Table 1. After that, the mixture was stirred at a liquid temperature of 160° C. to 220° C. for 12 hours. Water, which was generated during a heating reaction, was removed. The mixture was allowed to stand to cool to room temperature, and thus a complex polyester composition was obtained as a yellow transparent liquid material.

<Polyhydric Alcohol>

The polyhydric alcohol used in the example of the present invention is as follows.

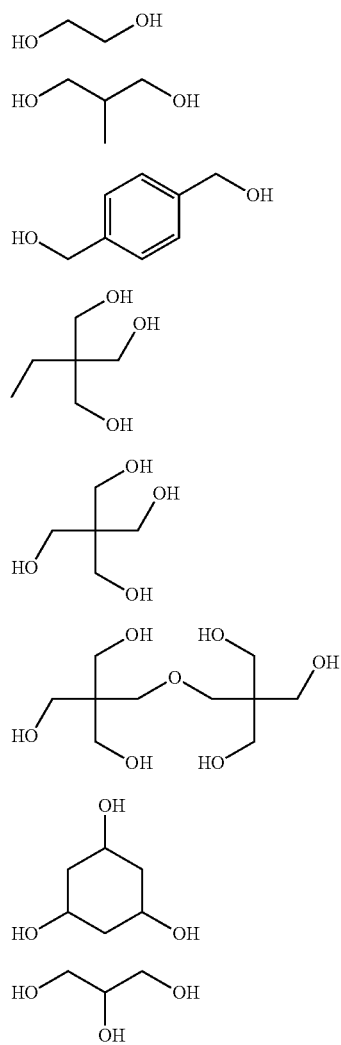

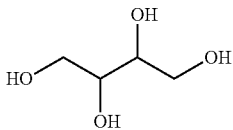
PA-19

<Monohydric Alcohol>

In addition, the monohydric alcohol used in the example of the present invention is as follows.

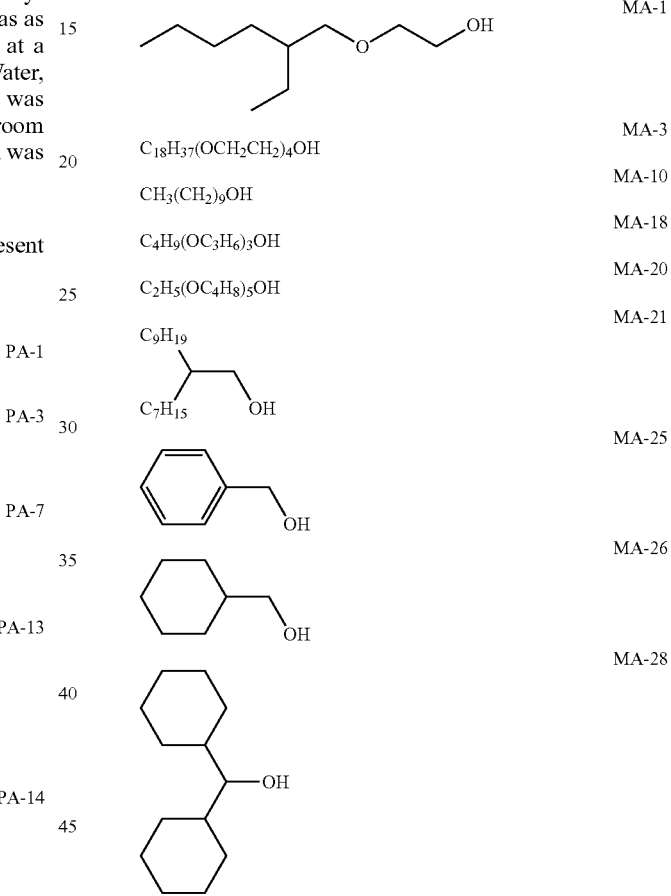

<Preparation of Lubricant>

The obtained complex polyester composition and mineral oil (100 neutral oil, and viscosity at 100° C. of 4.4 mm/s$^2$) were mixed at a mass ratio of 25/75, and thus lubricant containing 2.0 mass % of calcium sulfonate was prepared as a metal-based cleaning agent. The friction coefficient of the lubricant was measured by the following method.

<Evaluation>

Evaluation in which it was assumed that the lubricant was used under extreme pressure conditions was performed by measuring a friction coefficient using a vibration-type friction abrasion test machine (manufactured by Optimol Instruments Prueftechnik GmbH, and product name: SRV 4) at a vibration frequency of 100 Hz, an amplitude of 2.0 mm, a load of 30 N, a temperature of 65° C., a test piece: point contact (ball), and a test time of 30 minutes.

In general, the friction coefficient which was obtained by assuming that the lubricant was used under extreme pressure conditions was obtained as a value greater than that of the friction coefficient of a general fluid lubrication region or elastic fluid lubrication region. For this reason, a lubricant having a small friction coefficient under extreme pressure conditions and having excellent evaluation described below naturally has a small friction coefficient and excellent evaluation in a general fluid lubrication region or elastic fluid lubrication region. Furthermore, when the evaluation was higher than or equal to D Rank, the lubricant was considered as acceptable. The evaluation results of the friction coefficient of a SRV4 test machine in which extreme pressure conditions are assumed are shown in Table 1 described below.

A Rank: Friction Coefficient<0.050
B Rank: 0.050≤Friction Coefficient<0.055
C Rank: 0.055≤Friction Coefficient<0.060
D Rank: 0.060≤Friction Coefficient<0.070
E Rank: Friction Coefficient 0.070

In addition, the tint of the complex polyester composition was measured as transmittance at a wavelength of 450 nm by using water as a reference with a spectrophotometer (UV-3100PC, manufactured by Shimadzu Corporation), and evaluation was performed according to the following criteria. Furthermore, when the evaluation is higher than or equal to B Rank, the lubricant was considered as acceptable. The results are shown in Table 1 described below.

A Rank: Transmittance>95%
B Rank: 95% Transmittance>70%
C Rank: Transmittance 70%

Comparative Example 1

In Comparative Example 1, a friction coefficient and tint were measured by the same method as that in Example 1 except that a dilinolelyl diol dimer/dilinol dimer copolymer (Lusplan DD-DA7, manufactured by Nippon Fine Chemical Co., Ltd.) disclosed in Example 1 of JP2007-217414A was used instead of the polyester composition of Example 1. The results are shown in Table 1.

Comparative Example 2

In Comparative Example 2, a friction coefficient and tint were measured by the same method as that in Example 1 except that polyester disclosed in Production Example 1 of JP1996-208814A (JP-H08-208814A) was used instead of the polyester composition of Example 1. The results are shown in Table 1.

Comparative Example 3

In Comparative Example 3, polyester which was synthesized by bivalent fatty acid Pripol 1009 (Trademark) and dihydric fluoroalcohol disclosed in EXAMPLE 1 of U.S. Pat. No. 4,898,981A with reference to Example 1 of JP1995-501838A (JP-H07-501838A) was used instead of the polyester composition of Example 1. A friction coefficient and tint were measured by the same method as that in Example 1 except that the compound described above was used. The results are shown in Table 1.

Comparative Example 4

In Comparative Example 4, a friction coefficient and tint were measured by the same method as that in Example 1 except that a polyester composition disclosed in Example 40 of JP2011-89106A was used instead of the polyester composition of Example 1. The results are shown in Table 1.

TABLE 1

| | Mixing Amount of Erucic Acid Dimer (Parts by Mass) | Mixing Amount of Dimer Acid (Parts by Mass) | Polyhydric Alcohol | | Monohydric Alcohol | | Polyester Composition | Evaluation Result | |
|---|---|---|---|---|---|---|---|---|---|
| | | | Type | Mixing Amount (Parts by Mass) | Type | Mixing Amount (Parts by Mass) | | Friction Coefficient | Transmittance |
| Example 1 | 77 | — | PA-1 | 4 | MA-1 | 19 | PEC-1 | C | A |
| Example 2 | 78 | — | PA-1 | 4 | MA-10 | 18 | PEC-2 | D | A |
| Example 3 | 76 | — | PA-3 | 5 | MA-1 | 19 | PEC-3 | C | A |
| Example 4 | 82 | — | PA-3 | 5 | MA-25 | 13 | PEC-4 | D | A |
| Example 5 | 74 | — | PA-7 | 8 | MA-18 | 18 | PEC-5 | C | A |
| Example 6 | 72 | — | PA-7 | 7 | MA-28 | 21 | PEC-6 | D | A |
| Example 7 | 71 | — | PA-13 | 5 | MA-1 | 24 | PEC-7 | A | A |
| Example 8 | 54 | — | PA-13 | 4 | MA-20 | 42 | PEC-8 | A | A |
| Example 9 | 77 | — | PA-13 | 6 | MA-26 | 17 | PEC-9 | A | A |
| Example 10 | 73 | — | PA-13 | 5 | MA-10 | 22 | PEC-10 | A | A |
| Example 11 | 78 | — | PA-13 | 5 | MA-25 | 17 | PEC-11 | A | A |
| Example 12 | 73 | — | PA-14 | 4 | MA-1 | 23 | PEC-12 | A | A |
| Example 13 | 53 | — | PA-14 | 3 | MA-3 | 44 | PEC-13 | A | A |
| Example 14 | 65 | — | PA-14 | 3 | MA-21 | 32 | PEC-14 | A | A |
| Example 15 | 80 | — | PA-14 | 4 | MA-25 | 16 | PEC-15 | A | A |
| Example 16 | 71 | — | PA-14 | 4 | MA-28 | 25 | PEC-16 | A | A |
| Example 17 | 73 | — | PA-15 | 5 | MA-1 | 22 | PEC-17 | A | A |
| Example 18 | 57 | — | PA-15 | 4 | MA-20 | 39 | PEC-18 | A | A |
| Example 19 | 65 | — | PA-15 | 5 | MA-21 | 30 | PEC-19 | A | A |
| Example 20 | 75 | — | PA-15 | 5 | MA-10 | 20 | PEC-20 | A | A |
| Example 21 | 71 | — | PA-15 | 5 | MA-28 | 24 | PEC-21 | A | A |
| Example 22 | 71 | — | PA-16 | 5 | MA-1 | 24 | PEC-22 | A | A |
| Example 23 | 63 | — | PA-16 | 4 | MA-20 | 33 | PEC-23 | A | A |
| Example 24 | 73 | — | PA-16 | 5 | MA-10 | 22 | PEC-24 | B | A |
| Example 25 | 78 | — | PA-16 | 5 | MA-25 | 17 | PEC-25 | B | A |
| Example 26 | 72 | — | PA-17 | 3 | MA-1 | 25 | PEC-26 | A | A |
| Example 27 | 52 | — | PA-17 | 2 | MA-3 | 46 | PEC-27 | A | A |

TABLE 1-continued

| | Mixing Amount of Erucic Acid Dimer (Parts by Mass) | Mixing Amount of Dimer Acid (Parts by Mass) | Polyhydric Alcohol Type | Polyhydric Alcohol Mixing Amount (Parts by Mass) | Monohydric Alcohol Type | Monohydric Alcohol Mixing Amount (Parts by Mass) | Polyester Composition | Evaluation Result Friction Coefficient | Evaluation Result Trans- mittance |
|---|---|---|---|---|---|---|---|---|---|
| Example 28 | 79 | — | PA-17 | 4 | MA-26 | 17 | PEC-28 | A | A |
| Example 29 | 74 | — | PA-17 | 3 | MA-10 | 23 | PEC-29 | B | A |
| Example 30 | 73 | — | PA-19 | 3 | MA-1 | 24 | PEC-30 | A | A |
| Example 31 | 80 | — | PA-19 | 4 | MA-26 | 16 | PEC-31 | A | A |
| Example 32 | 80 | — | PA-19 | 4 | MA-25 | 16 | PEC-32 | B | A |
| Example 33 | 71 | — | PA-19 | 3 | MA-28 | 26 | PEC-33 | B | A |
| Example 38 | 38 | 31 | PA-13 | 5 | MA-1 | 26 | PEC-34 | A | B |
| Example 39 | 11 | 37 | PA-13 | 4 | MA-3 | 48 | PEC-35 | A | B |
| Example 40 | 44 | 9 | PA-13 | 4 | MA-20 | 43 | PEC-36 | A | B |
| Example 42 | 70 | 7 | PA-13 | 5 | MA-26 | 18 | PEC-37 | A | B |
| Comparative Example 1 | — | — | — | — | — | — | PEC-38 | E | A |
| Comparative Example 2 | — | — | — | — | — | — | PEC-39 | E | B |
| Comparative Example 3 | — | — | — | — | — | — | PEC-40 | E | C |
| Comparative Example 4 | — | — | — | — | — | — | PEC-41 | B | C |

As known from Table 1, it is found that the friction coefficient of the lubricant using the complex polyester composition of the example under extreme pressure conditions is suppressed to be low. Furthermore, according to this, it is assumed that in the lubricant using the complex polyester composition of the example, the friction coefficient in a general fluid lubrication region or elastic fluid lubrication region is suppressed to be low. That is, the lubricant using the complex polyester composition of the example is able to exhibit excellent lubrication performance under general conditions, as well as under extreme pressure conditions.

In addition, it is found that a complex polyester composition having high transmittance and high transparency is able to be obtained according to the complex polyester composition of the example.

In contrast, it is found that the friction coefficient of the lubricant using the complex polyester composition of Comparative Examples 1 to 3 increases under extreme pressure conditions. That is, the lubricant using the complex polyester composition of Comparative Examples 1 to 3 is not able to exhibit excellent lubrication performance under extreme pressure conditions. In addition, it is found that a complex polyester composition having low transmittance and low transparency is obtained according to the complex polyester composition of Comparative Examples 3 and 4.

INDUSTRIAL APPLICABILITY

According to the present invention, it is possible to obtain a complex polyester composition which is able to exhibit high lubrication performance even when under extreme pressure conditions. Further, when the complex polyester composition of the present invention is used, it is possible to obtain a lubricant having high transparency, and it is possible to easily determine the degree to which the deterioration of the lubricant has progressed or whether or not foreign substances are mixed into the lubricant. For this reason, the complex polyester composition of the present invention has excellent usability, and is preferably used as a lubricant in various applications, and thus has high industrial applicability.

What is claimed is:

1. A complex polyester composition containing polyester obtained by condensing
polyhydric alcohol having at least two hydroxyl groups,
a dicarboxylic acid having 44 carbon atoms, and
monohydric alcohol.

2. The complex polyester composition according to claim 1, wherein the dicarboxylic acid having 44 carbon atoms is an erucic acid dimer.

3. The complex polyester composition according to claim 1, wherein the polyhydric alcohol has three or more hydroxyl groups.

4. The complex polyester composition according to claim 1, wherein the polyhydric alcohol is selected from pentaerythritol, trimethylol propane, glycerin, and dipentaerythritol.

5. The complex polyester composition according to claim 1, wherein the monohydric alcohol is denoted by General Formula (1) described below, and

$$R^a\!-\!\!\left(\!O(CX^{a1}X^{a2})_{na1}\!\right)_{\!na2}\!OH \qquad \text{General Formula (1)}$$

in General Formula (1), $R^a$ represents an alkyl group which may have a substituent group, a cycloalkyl group which may have a substituent group, an alkenyl group which may have a substituent group, an aryl group which may have a substituent group, or a heteroaryl group which may have a substituent group, $X^{a1}$ and $X^{a2}$ each independently represent a hydrogen atom, a halogen atom, or an alkyl group, na1 represents an integer of 2 to 4, and na2 represents an integer of 1 to 12.

6. The complex polyester composition according to claim 1, wherein the complex polyester composition contains polyester obtained by further condensing a dimer acid in addition to the polyhydric alcohol, the dicarboxylic acid having 44 carbon atoms, and the monohydric alcohol.

7. The complex polyester composition according to claim 1, wherein the complex polyester composition contains polyester obtained by further condensing a trimer acid in addition to the polyhydric alcohol, the dicarboxylic acid having 44 carbon atoms, and the monohydric alcohol.

8. The complex polyester composition according to claim 1, wherein at least one type of polyester is denoted by General Formula (2) described below, and

 General Formula (2)

in General Formula (2), R represents a n-valent atomic group, $R^1$ represents a residue of a dicarboxylic acid having 44 carbon atoms, $R^2$ represents an alkyl group which may have a substituent group, a cycloalkyl group which may have a substituent group, an alkenyl group which may have a substituent group, an aryl group which may have a substituent group, or a heteroaryl group which may have a substituent group, and n represents an integer of 2 to 6.

9. The complex polyester composition according to claim 8, wherein in General Formula (2) described above, n represents an integer of 3 to 6.

10. The complex polyester composition according to claim 8, wherein in General Formula (2) described above, R represents an atomic group formed of saturated aliphatic hydrocarbon which may have a substituent group.

11. The complex polyester composition according to claim 8, wherein in General Formula (2) described above, the number of carbon atoms of $R^2$ is greater than or equal to 4.

12. The complex polyester composition according to claim 8, wherein in General Formula (2) described above, $R^2$ represents a group having an oxyalkylene structure.

13. The complex polyester composition according to claim 1, wherein viscosity at 40° C. is 50 mPa·s to 1650 mPa·s.

14. A lubricant composition containing the complex polyester composition according to claim 1, and at least one type of additive selected from an abrasion preventing agent, a viscosity index improver, an antioxidant, a cleaning agent, a dispersant, a fluidizing agent, a curing agent, a corrosion preventing agent, a seal compatible agent, a defoaming agent, a rust preventing agent, a friction adjuster, and a thickener.

15. A lubricant composition containing at least the complex polyester composition according to claim 1, and at least one type of medium selected from mineral oil, a fatty oil compound, polyolefin oil, silicone oil, perfluoropolyether oil, diphenyl ether oil, aromatic ester oil, aliphatic monoester oil, aliphatic diester oil, and polyol ester lubricating oil.

16. A lubricant containing the complex polyester composition according to claim 1.

17. The lubricant according to claim 16, wherein the lubricant is used as lubricating oil for grease, a releasing agent, engine oil for an internal combustion engine, oil for metal working (machining), oil for a bearing, fuel for a combustion engine, vehicle engine oil, gear oil, operating oil for an automobile, lubricating oil for a vessel and an aircraft, machine oil, turbine oil, hydraulic operating oil, compressor and vacuum pump oil, freezer oil, lubricating oil for metal working, a lubricant for magnetic recording medium, a lubricant for a micro machine, a lubricant for an artificial bone, shock absorber oil, or rolling oil.

18. A production method for a complex polyester composition, comprising:
obtaining a mixture by mixing polyhydric alcohol having at least two hydroxyl groups, a dicarboxylic acid having 44 carbon atoms, and monohydric alcohol; and
performing dehydration condensation with respect to the mixture.

19. The production method for a complex polyester composition according to claim 18, wherein the aforementioned obtaining the mixture is mixing the polyhydric alcohol, the dicarboxylic acid having 44 carbon atoms, and the monohydric alcohol such that an equivalence ratio of mixing the dicarboxylic acid having 44 carbon atoms with respect to the polyhydric alcohol is 1 to 3, and an equivalence ratio of mixing the monohydric alcohol with respect to the polyhydric alcohol is 0.5 to 3.

20. The production method for a complex polyester composition according to claim 18, wherein the aforementioned performing the dehydration condensation includes adding a hydrocarbon-based solvent having a boiling point of 110° C. to 160° C. in the amount of 1 mass % to 25 mass % with respect to the mixture, and of performing the dehydration condensation while setting water in an azeotropic state.

21. The production method for a complex polyester composition according to claim 18, wherein the aforementioned performing the dehydration condensation is performing condensation in the absence of a solvent.

22. The complex polyester composition according to claim 1, wherein said dicarboxylic acid having 44 carbon atoms is used as a sole dicarboxylic acid for condensation to produce the polyester.

* * * * *